United States Patent [19]

Suemori et al.

[11] Patent Number: 5,523,220

[45] Date of Patent: Jun. 4, 1996

[54] METHOD FOR PRODUCING 3,4-DIHYDROXYPHTHALIC ACID

[75] Inventors: Akio Suemori; Ryuichiro Kurane; Kenji Nakajima; Yoshihiro Nakamura, all of Tsukuba, Japan

[73] Assignee: Director-General of Agency of Industrial Science and Technology, Tokyo, Japan

[21] Appl. No.: 407,634

[22] Filed: Mar. 21, 1995

[30] Foreign Application Priority Data

Mar. 31, 1994 [JP] Japan .................... 6-087897

[51] Int. Cl.$^6$ .................... C12P 7/44; C12P 7/42
[52] U.S. Cl. .................... 435/142; 435/252.1; 435/146
[58] Field of Search .................... 435/142, 252.1, 435/146

[56] References Cited

U.S. PATENT DOCUMENTS 5,135,858  8/1992  Yamada et al. .................... 435/142

FOREIGN PATENT DOCUMENTS 0360407   3/1990  European Pat. Off. .............. 435/142
2-100683  4/1990  Japan .
2100690   4/1990  Japan .................... 435/142
2-149540  6/1990  Japan .
3076589   4/1991  Japan .................... 435/142

OTHER PUBLICATIONS

Eaton et al "Jour of Bacteriol" Jul. 1982 vol. 151, No. 1 pp. 48–57 Metabolism of Dibutylphthalate & Phthalate by Micrococcus sp. Strain 12B.

*Primary Examiner*—Herbert J. Lilling
*Attorney, Agent, or Firm*—Birch, Stewart, Kolasch & Birch

[57] ABSTRACT

There is disclosed a method for producing 3,4-dihydroxyphthalic acid, comprising treating phthalic acid with a product which is obtained by treating the cell membrane fraction of microorganism bacterial bodies capable of converting phthalic acid to 3,4-dihydroxyphthalic acid with a condensate of polyethylene oxide with a higher alcohol, thereby converting the phthalic acid to 3,4-dihydroxyphthalic acid. According to the method, only 3,4-dihydroxyphthalic acid, which is an intermediary metabolite, can be produced efficiently in a process of biodegrading phthalic acid with a microorganism.

5 Claims, No Drawings

METHOD FOR PRODUCING 3,4-DIHYDROXYPHTHALIC ACID

FIELD OF THE INVENTION

The present invention relates to a method for producing 3,4-dihydroxyphthalic acid.

BACKGROUND OF THE INVENTION

Since 3,4-dihydroxyphthalic acid is a useful monomer as a raw material of various functional polymer materials, it is used in various fields of chemical industries.

To introduce hydroxyl groups specifically to the 3- and 4-positions of phthalic acid is very important in polymerization for the use of this material (3,4-dihydroxyphthalic acid). This is because, if only a small amount of a by-product in which hydroxyl groups have been introduced onto the 3- and 5-positions is existing with 3,4-dihydroxyphthalic acid, the polymerization reaction is stopped by that by-product, and a material having a satisfactory molecular weight and molecular length cannot be obtained, thereby increasing the possibility that the desired function will be adversely influenced.

To produce 3,4-dihydroxyphthalic acid, a chemical synthesis technique is taken into consideration, but the synthesis process is complicated. In particular, in the synthesis, it is difficult to introduce hydroxyl groups specifically to the adjacent 3- and 4-positions. By a method wherein the desired product is obtained as an intermediary metabolite by biodegrading phthalic acid with a microorganism, the desired product wherein hydroxyl groups have been introduced specifically onto the 3- and 4-positions can be obtained. However, the method has a problem due to living cells, which is that further decomposition occurs owing to an enzyme present in the living cells. Therefore the particular substance desired cannot be obtained efficiently. The microorganism capable of converting phthalic acid to 3,4-dihydroxyphthalic acid is described in Eaton, R. W. & Ribbons, D. W. (1982) *J. Bacteriol.*, 151, 48–57.

Accordingly, under the existing circumstances, a method for efficiently obtaining only 3,4-dihydroxy-phthalic acid is needed.

SUMMARY OF THE INVENTION

The object of the present invention is to provide a method for efficiently producing 3,4-dihydroxyphthalic acid, and more particularly to a method for producing only 3,4-dihydroxyphthalic acid, which is an intermediary metabolite, efficiently in a process of biodegrading phthalic acid with a microorganism.

Other and further objects, features, and advantages of the invention will appear more fully from the following description.

DETAILED DESCRIPTION OF THE INVENTION

The inventors have keenly studied in various ways to solve the above problems. As a result of studying, we have found that, when the cell membrane of microorganism bacterial body capable of converting phthalic acid to 3,4-dihydroxyphthalic acid is treated with a condensate of polyethylene oxide with a higher alcohol, and then the resulting treated product is allowed to act on phthalic acid to carry out biodegrading the phthalic acid, only 3,4-dihydroxyphthalic acid, which is an intermediary metabolite, can be produced efficiently. The present invention has been completed base on the above findings.

That is, the present invention is a method of obtaining 3,4-dihydroxyphthalic acid, which is an intermediary metabolite, in a step of biodegrading phthalic acid with a microorganism. In the method, the membrane fraction of the microorganism bacterial body, which fraction is treated with a condensate of polyethylene oxide with a higher alcohol, is used. By the treatment, the native existing enzyme included in the cell membrane, which enzyme decomposes 3,4-dihydroxyphthalic acid further (hereinafter referred to as the included enzyme), is solubilized specifically from the cell membrane (is removed to outside the membrane) and is fractionated from the intended enzymes group that produces 3,4-dihydroxyphthalic acid (hereinafter referred to as the intended enzymes). Then, the thus treated product is allowed to act on phthalic acid, to efficiently produce only 3,4-dihydroxyphthalic acid.

In the process of biodegradation with bioorganisms from phthalic acid to protocatechuic acid through 3,4-dihydroxyphthalic acid, three enzymes: phthalic acid 3,4-dioxygenase, 3,4-dihydro-3,4-dihydroxyphthalic acid 3,4-dihydrogenase, and 3,4-dihydroxyphthalic acid 2 decarboxylase, are involved. Out of these three enzymes, the treatment of the membrane fraction with a condensate of polyethylene oxide with a higher alcohol solubilizes (removes to outside the membrane) specifically only the included enzyme (specifically, 3,4-dihydroxyphthalic acid 2 decarboxylase) that participates in the further reaction of causing 3,4-dihydroxyphthalic acid to be decomposed. Therefore, by causing the intended enzymes that have remained in the membrane after the treatment, which enzymes participate in the reaction of producing 3,4-dihydroxyphthalic acid (specifically, phthalic acid 3,4-dioxygenase and 3,4-dihydro-3,4-dihydroxyphthalic acid 3,4-dihydrogenase), to act on phthalic acid, only 3,4-dihydrophthalic acid can be produced in a high yield.

in the present invention, the expression "a microorganism bacteria capable of converting phthalic acid to 3,4-dihydroxyphthalic acid" means a microorganism into which the above enzymes that biodegrade phthalic acid have been induced by growing microorganism bacterial bodies in a completely synthetic medium that uses phthalic acid as the sole carbon source. The microorganism bacterial bodies into which the enzymes have been thus induced are subjected to an ultrasonic treatment, for separation into a cell-free enzyme liquid and a membrane fraction; the membrane fraction is suspended in a phosphate buffer, the Good buffer, or the like, and a condensate of polyethylene oxide with a higher alcohol is added to the suspension and the resultant reaction is allowed to proceed, so that only the included enzyme in the membrane fraction is specifically solubilized.

Herein, the condensate of polyethylene oxide with a higher alcohol includes condensates of polyethylene oxide, preferably condensates of polyethylene glycols(8 to 30), with a higher alcohol, preferably a lauryl alcohol, a cetyl alcohol, an oleyl alcohol, and the like. A polyethylene(20) cetyl ether (trade name: Brij 58, manufactured by ICI) is used more preferably.

Further, the condensate of polyethylene oxide with a higher alcohol is used at a concentration of 0.05 to 2% by weight, preferably about 0.1% by weight; and the amount to be added is, for example, 500 to 2,000% (w/w), preferably about 1,000% (w/w), to the membrane fraction.

The membrane fraction is treated with the condensate at 0° to 10° C., preferably at about 5° C., for 6 to 48 hours, preferably about 24 hours, with stirring.

The microorganism that can be applied may be microorganisms of the genera and species of any of bacteria, yeasts, molds, and the like that can produce the particular substances, and preferable examples are gram-positive bacteria, such as Rhodococcus, Micrococcus, Staphylococcus, Streptococcus, Leuconstoc, Ruminococcus, Bacillus, Clostridium, and Lactobacillus, with Phodococcus genus bacteria particularly preferable.

The treated product obtained in the above manner is used to carry out the conversion reaction of phthalic acid, which serves as a substrate.

Preferably, the conversion reaction is carried out in a 5- to 50-mM phosphate buffer (pH: 6.5 to 8.5) at 24° to 36° C. under conditions of phthalic acid being 0.1 to 5 mM, NADH being 0.1 to 5 mM, $NAD^+$ being 0.1 to 5 mM, and the treated product being 0.5 to 3 mg/ml. More preferably, the conversion reaction is carried out in a 10-mM phosphate buffer (pH: 7.1) at 30° C. under conditions of phthalic acid being 1 mM, NADH being 3 mM, $NAD^+$ being 3 mM, and the treated product being 1 mg/ml.

When the conversion reaction of phthalic acid using the above treated product is carried out in the presence of metal ions, preferably manganese ions, zinc ions, iron ions, or the like, the conversion reaction can be remarkably promoted.

According to the method of the present invention, 3,4-dihydroxyphthalic acid that is a monomer useful as a raw material of functional polymer materials, can be produced efficiently in a process of biodegrading phthalic acid with a microorganism.

Now the present invention will be described in more detail with reference to the following Examples, but the present invention is in no way limited by these Examples.

Example 1

(1) Cultivation of Rhodococcus erythropolis and Induced Production of Enzymes

*Rhodococcus erythropolis* KR-S-1 was pre-cultured at 30° C. for 1 day using a completely synthetic medium, in which para-hydroxybenzoic acid was the sole carbon source. A sufficient amount of grown bacterial bodies was recovered, washed, and suspended in a completely synthetic medium, in which phthalic acid was the sole carbon source. The suspension was cultured at 30° C. for about 3 to 4 days, and the bacterial bodies at the logarithmic growth phase were recovered and washed. As accession number FERM BP-4913, this *Rhodococcus erythropolis* KR-S-1 was deposited in the National Institute of Bioscience and Human-Technology of the Agency of Industrial Science and Technology, at 1-3, Higasi 1-chome, Tsukuba-shi, Ibaraki-ken, 305, Japan. This bacteria was deposited on May 1, 1981 as the date of the original deposit, and the deposit was made in accordance with the Budapest treaty. All restrictions on the availability to the public of the deposited materials will be irrevocably removed upon the granting of a patent.

(2) Solubilization of the Enzyme

The phthalic acid-grown bacterial bodies were subjected to an ultrasonic treatment, for separation into a membrane fraction and a cell-free enzyme liquid. The prepared membrane fraction was suspended in a 10-mM phosphate buffer (pH: 7.1; and containing 10% (v/v) of glycerol), so that the membrane fraction was 10 mg/ml. Then various chemical reagents and surface-active agents shown in Table 1 were added to the suspension, followed by stirring at 4° C. for 24 hours, to solubilize the enzyme from the membrane fraction.

(3) Production of 3,4-Dihydroxyphthalic Acid Using the Treated Product

Each of the treated products obtained in (2) above was used to carry out a conversion reaction with phthalic acid as a substrate, and the produced substance was studied. The conversion reaction was carried out at 30° C. in a 10-mM phosphate buffer (pH: 7.1), under conditions of phthalic acid being 1 mM, NADH being 3 mM, $NAD^+$ being 3 mM, and the treated product being 1 mg/ml. The results are shown in Table 1. In the case without the treatment, protocatechuic acid was obtained as an end product. In the cases wherein the treatment with Tween 80 (polyoxyethylene (20) sorbitan mono-oleate); trade name, manufactured by Atlas Powder) or Triton X-100 (polyethylene glycol p-isooctylphenyl ether (octoxynol); trade name, manufactured by Rohm & Haas) was carried out, converted products other than phthalic acid were not detected. This is because, in the cases of Tween 80 and Triton X-100, the degree of solubilization of phthalic acid 3,4-oxygenase, which was the intended enzyme, was large, and 3,4-dihydroxyphthalic acid was not produced. On the other hand, when the product treated with Brij 58 was used, as an end product a substance other than protocatechuic acid was detected, and the substance was separated, -purified, and identified as 3,4-dihydroxyphthalic acid. That is, it is considered that, when the product treated with Brij 58 is used, out of the three enzymes involved in the reaction for the conversion of phthalic acid to protocatechuic acid, only the 3,4-dihydroxyphthalic acid 2 decarboxylase, which is an included enzyme, is solubilized specifically, and the other two enzymes, which are the intended enzymes, remain in the membrane.

TABLE 1

Conversion of Phthalic Acid with Treated Products and Identification of the Obtained Product

| Method for treating (used chemical reagents etc.) | Reaction time (hours) | Relative mobility of the spot obserbed in thin-layer chromatography | Substance |
|---|---|---|---|
| without treating | 2 | 0.18 | 3,4-Dihydroxyphthalic acid |
|  |  | 0.41 | Phthalic acid |
|  |  | 0.69 | Protocatechuic acid |
| 500 mM KCL 10 mM EDTA | 24 | 0.69 | Protocatechuic acid |
| 0.1% by weight Brij 58 | 2 | 0.18 | 3,4-Dihydroxyphthalic acid |
|  |  | 0.41 | Phthalic acid |
|  | 4 | 0.18 | 3,4-Dihydroxyphthalic acid |
|  |  | 0.41 | Phthalic acid |
|  | 24 | 0.18 | 3,4-Dihydroxyphthalic acid |
| 0.1% by weight Tween 80 | 24 | 0.41 | Phthalic acid |
| 0.1% by weight Triton X-100 | 24 | 0.41 | Phthalic acid |

Example 2

Influence of Metal Ions on Production of 3,4-Dihydroxyphthalic Acid

The influence of metal ions on the conversion from phthalic acid to 3,4-dihydroxyphthalic acid using the product treated with Brij 58 was measured (Table 2). Manganese ions, zinc ions, and iron ions exhibited a remarkable action for facilitation of the conversion reaction.

TABLE 2

Influence of Metal Ions on the Production
of 3,4-Dihydroxyphthalic Acid Obtained by
Using the Product Treated with Brij 58

| Metal ion | Amount of produced 3,4-dihydroxyphthalic acid (%) |
|---|---|
| $Mn^{2+}$ | 328 |
| $Fe^{2+}$ | 314 |
| $Zn^{2+}$ | 228 |
| $Fe^{3+}$ | 196 |
| $Ca^{2+}$ | 115 |
| $Mg^{2+}$ | 106 |
| $Pb^{2+}$ | 75 |
| Control | 100 |

Having described our invention as related to the present embodiments, it is our intention that the invention not be limited by any of the details of the description, unless otherwise specified, but rather be construed broadly within its spirit and scope as set out in the accompanying claims.

What we is claimed is:

1. A method for producing 3,4-dihydroxyphthalic acid, comprising treating phthalic acid, with a treated membrane substance which is obtained by treating the cell membrane fraction of the bacteria *Rhodococcus erythropolis* KR-S-1 whose accession number is FERM BP-4913 that is capable of converting phthalic acid to 3,4-dihydroxyphthalic acid with a condensate of polyethylene oxide with a higher alcohol, and converting the phthalic acid to 3,4-dihydroxyphthalic acid.

2. The method as claimed in claim 1, wherein the condensate of polyethylene oxide with a higher alcohol is polyethylene(20) cetyl ether.

3. The method as claimed in claim 1, wherein the treated membrane substance is one that is obtained by adding to the cell membrane fraction, 500 to 2,000% (w/w) of a condensate of polyethylene oxide with a higher alcohol, in an concentration of 0.05 to 2% by weight, and treating the cell membrane fraction for 6 to 48 hours.

4. The method as claimed in claim 1, wherein the conversion to 3,4-dihydroxyphthalic acid is carried out in the presence of metal ions, to promote the conversion.

5. The method as claimed in claim 4 wherein the metal ion is either a manganese ion, a zinc ion, or an iron ion.

* * * * *